United States Patent [19]
Hölbl et al.

[11] Patent Number: 5,161,446
[45] Date of Patent: Nov. 10, 1992

[54] MICROTOME

[75] Inventors: Werner Hölbl, Vienna, Austria; Gernot Hänsel, Stuttgart, Fed. Rep. of Germany

[73] Assignee: Leica Instruments GmbH, Nussloch, Fed. Rep. of Germany

[21] Appl. No.: 776,983

[22] Filed: Oct. 15, 1991

[30] Foreign Application Priority Data

Oct. 19, 1990 [DE] Fed. Rep. of Germany ....... 4033335

[51] Int. Cl.[5] .................................................. G01N 1/06
[52] U.S. Cl. ...................................... 83/703; 83/410.8; 83/414; 83/915.5
[58] Field of Search ............... 83/915.5, 397, 410.8, 83/411.4, 412, 414, 464, 544, 522.19, 648, 703, 856, 411.3

[56] References Cited

U.S. PATENT DOCUMENTS

| | | | |
|---|---|---|---|
| 3,564,961 | 2/1971 | Burkhardt | 83/412 |
| 3,733,948 | 5/1973 | Pickett | 83/915.5 X |
| 3,771,405 | 11/1973 | Blum | 83/714 |
| 3,828,641 | 8/1974 | Sitte | 83/703 |
| 3,981,214 | 9/1976 | Wich | 83/414 |
| 4,126,069 | 11/1978 | Shimonaka | 83/703 |
| 4,494,444 | 1/1985 | Masse | 83/648 X |
| 4,505,175 | 3/1985 | Reichel | 83/703 |
| 4,594,929 | 6/1986 | Behme et al. | 83/915.5 X |
| 4,625,608 | 12/1986 | Behme et al. | 83/915.5 X |
| 4,967,629 | 11/1990 | Behme | 83/714 |

Primary Examiner—Douglas D. Watts
Assistant Examiner—Eugenia A. Jones
Attorney, Agent, or Firm—Bean, Kauffman & Spencer

[57] ABSTRACT

In order that biological and histological sections may be produced without the risk of injury and at an expenditure acceptable for hobby and instructional purposes, a specimen arm whose distal end carries a specimen holder is supported on the base plate of the microtome. The specimen arm is attached to the base by a spindle which is mounted on the base plate such that it can be displaced in the direction of the cutting knife. An adjusting member is provided for adjusting the position of displacement of the spindle. Uniform section thicknesses are facilitated by a locking ball received in the adjusting member. A clamp is provided on the base plate for holding commercially available cutting blades at the required clearance angle of the cutting edge. Movement of the specimen arm can be brought about by means of a handle or a crank. When the specimen arm is tilted away, unintentional contact with the cutting edge is prevented by a movable blade guard.

26 Claims, 4 Drawing Sheets

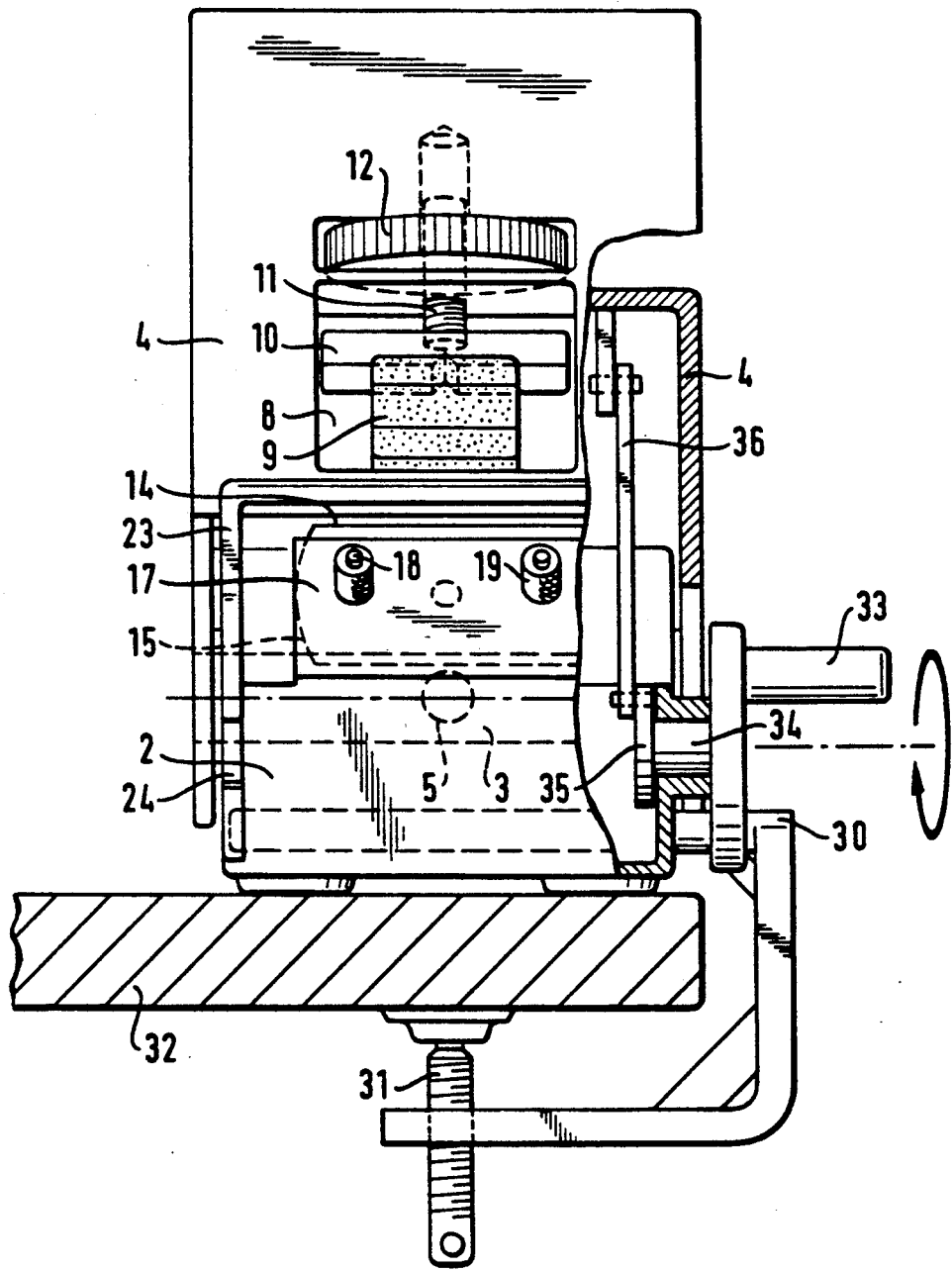

MICROTOME

BACKGROUND OF THE INVENTION

The invention relates to a microtome comprising a specimen holding means adapted to be reciprocally movable upwardly and downwardly in the plane of a stationary cutting knife, perpendicular to the cutting edge of the knife and mounted on a base plate so that it can be displaced in the direction of the cutting knife for adjustment of the thickness of specimen sections.

Such a microtome is disclosed in U.S. Pat. No. 4,691,151, inter alia. Such microtomes are used for removing thin, readily transilluminable layers, so-called sections, from biological and histological materials for light-microscopy examination thereof. To improve the quality of the cut in such microtomes, the specimen is typically embedded in paraffin or plastic.

Microtomes intended for the professional field are usually pieces of high-precision equipment which are too complex and expensive to be used for hobby, teaching and instructional purposes. On the other hand, the cutting of specimens with a razor blade does not often produce the desired cutting results and entails a great risk of injury.

It is therefore one object of the present invention to improve a microtome of the aforementioned type such that it can be used to produce sections of sufficiently uniform thickness for hobby and instructional purposes at an acceptable monetary expenditure and without putting the operator at risk of injury.

SUMMARY OF THE INVENTION

In accordance with the present invention, a microtome is provided having a specimen arm which includes a specimen holding means at one end thereof, the other end of the specimen arm being mounted to a base plate via a spindle, the spindle being adjustably supported on the base plate so that it can be displaced in the direction of the cutting knife. An adjusting means is provided for adjusting the position of the spindle.

To accomplish this, the spindle which supports the specimen arm is adjustably supported within elongated holes which are provided in the base plate. A threaded screw is rotatably supported in the base plate and has an adjustment knob at one end thereof, the other end of the screw threadably engaging the spindle. To compensate for play a spring is advantageously interposed between the spindle and the base plate. To provide for smooth movement of the threaded spindle, ball bearings may be provided to support the threaded screw which engages the spindle.

In order that several sections of uniform thickness can be cut in quick succession, a locating means is provided to facilitate movement of the specimen arm in predetermined increments. For example, spherical depressions may be arranged in a circular pattern on the base, in spaced relation to the adjustment knob, and a ball may be located in the adjustment knob, the ball being biased outwardly toward the base such that when the knob is rotated, the ball is urged into and travels in the circular pattern and enters the depressions as the knob rotates. The depressions may be spaced apart from one another a predetermined distance so that rotation of the knob from one depression to another will result in a particular distance of travel by the spindle, and thus the specimen arm, toward the knife blade. For example, the depressions may be spaced a distance which corresponds to a linear displacement of the spindle of 5 $\mu$m.

A knife holding means is provided which is suitable for receiving a commercial razor blade. The knife holding means comprises a pressure plate for holding the blade against a supporting surface and positions the blade at an incline relative to the path of movement of the specimen, the amount of angle being dictated by the amount of clearance required to achieve a proper section. The blade and the pressure plate are mounted on locating pins which extend through the blade and pressure plate. The pressure plate is fastened via knurled nuts screwed onto the ends of the locating pins. Preferably the pressure plate is wedge-shaped, with the edge of the wedge facing the specimen, to facilitate removal of sections.

A blade guard may be pivotally mounted on the base plate, and biased by a spring so that it rests against the specimen arm and thus covers the cutting edge when the specimen arm is located in its upward position.

The specimen arm is normally urged upwardly by the force of a spring, thus locating the specimen arm away from the knife holding means when the specimen arm is at rest. A handle may be provided on the distal end of the specimen arm for manually urging the specimen arm downwardly during cutting operations. Alternatively, a manually operable crank may be rotatably mounted on the base plate, the crank being drivingly connected to the specimen arm via a connecting linkage.

At the distal end of the specimen arm, a recess is provided for receiving the specimen to be cut. A holding plate is adjustably supported in the recess by a threaded shaft threadably disposed therethrough. The other end of the threaded shaft is in turn threadably mounted in a rotatable knurled disk, the knurled disk is rotatably retained within the distal end of the specimen. Consequently, by appropriately rotating the knurled disk, the holding plate may be tightened against the specimen to hold the specimen in its appropriate position.

To facilitate operation of the microtome, a bore may be provided on the base plate, into which the connecting attachment arm of a screw clamp may be inserted for fastening of the microtome.

Further features and advantages of the invention can be derived from the specification and drawings, where two embodiments are described.

BRIEF DESCRIPTION OF THE DRAWINGS

The nature and mode of operation of the present invention will now be more fully described in the following detailed description taken with the accompanying drawings, in which:

FIG. 1A is an enlarged detail of the portion of the microtome in circle IA of FIG. 1.

FIG. 4 is a front view of the microtome illustrated in FIG. 3.

DETAILED DESCRIPTION

Figure 1:
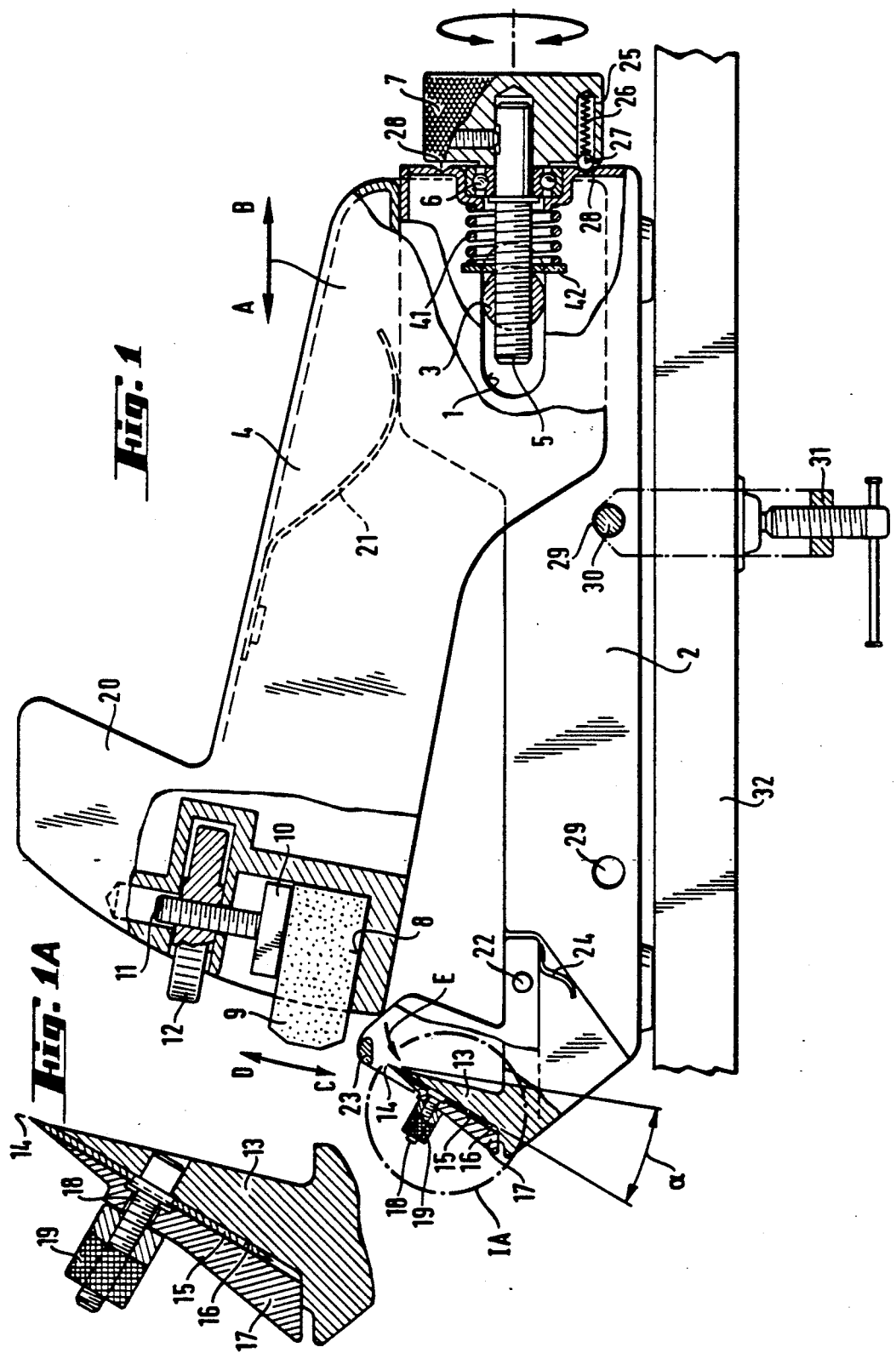
FIG. 1 is a partly sectional side view of a student microtome in accordance with the present invention.
Figure 2:
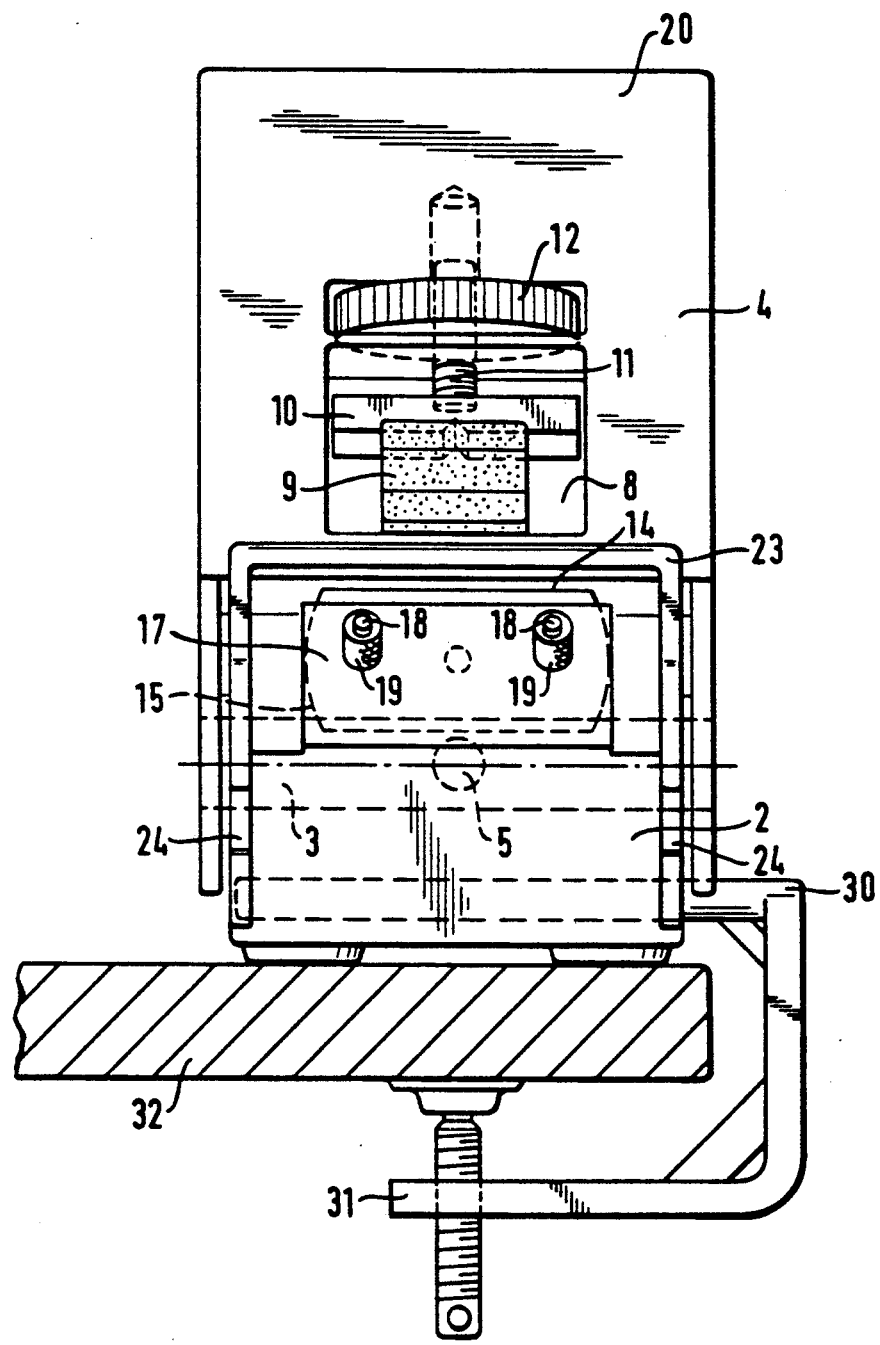
FIG. 2 is a front view of the microtome illustrated in FIG. 1.

Reference is now made more particularly to FIGS. 1 and 2, wherein a student microtome according to the present invention is illustrated, in which an elongated slot 1 is provided, within a horizontally disposed base plate 2, for supporting a spindle 3 which pivotally attaches a specimen arm 4 to the base plate 2. As shown in FIG. 1, a the base 2 may be designed to include a pair of spaced, parallel members which extend upwardly, each of the members having an elongated slot 1 therein which is adapted to receive the spindle 3. A threaded screw 5 may be provided, one end of which is threadably and rotatably retained within the spindle 3, the other end being supported by a plurality of ball bearings 6 which are in turn supported within a cylindrical cavity in the base plate 2. The ball bearings 6 provide minimized radial play and smooth rotation of the screw 5. Any residual play of the spindle 3 in the elongated slots 1 is eliminated by a spring 41 which is provided in the base plate 2 and acts against the spindle 3, biasing the spindle 3 towards the front of the microtome. The spring 41 is positioned over the threaded screw 5 and rests against the spindle 3 via a washer 42, which preferably is machined to close tolerances.

Attached to the end portion of the threaded screw 5 projecting from the base plate is a knurled adjustment knob 7. By turning the adjustment knob 7 the spindle 3 can be displaced in the direction of arrows A—B.

On the front end portion of the specimen arm 4 supported on the spindle 3 there is a recess 8 for receiving and holding a specimen 9. A threaded shaft is provided which extends from the specimen arm so that one end of the shaft 11 extends into the recess 8, where the end attaches to a pressure member 10. The other end of the threaded shaft 11 is threadably supported by a threaded nut 12 which is rotatably supported within the specimen arm 4. The outer periphery of the threaded nut 12 extends out of the body of the specimen arm 4, and is knurled to facilitate rotation thereof. In this way, the pressure member 10 is movably supported within the recess 8, and may be moved downwardly by appropriate rotation of the threaded nut 12, thus clamping the specimen 9 against the recess 8.

A wedge-shaped projection 13 extends from the base plate 2. A supporting surface 16 is provided on the projection 13 for mounting a commercial razor blade 15. Typically the razor blade is positioned at an oblique angle relative to the specimen arm. The supporting surface 16 and the direction of movement C—D of the specimen arm 4 and the specimen 9 attached thereto define an angle $\alpha$ which corresponds to the angle of the cutting edge 14 on the specimen 9 required for a proper cut. The razor blade 15 and a pressure plate 17 are placed over a pair of locating pins 18 located to correspond to the location of mounting holes located in the pressure plate 17 and mounting holes located in the commercial razor blades. The upper edge of the pressure plate preferably tapers toward the base 2, as shown in the drawings. The end portions of at least one, and preferably both of the locating pins 18 are provided with threads onto which knurled nuts 19 may be screwed. The knurled nuts may be tightened over the razor blade 15 and the pressure plate 17, thereby clamping them to the supporting surface 16.

On the upper side of the specimen arm 4, near the end which receives the specimen 9, a handle 20 is provided which may be grasped to move the specimen arm 4 upwardly and downwardly in the substantially vertical direction indicated by the arrows C—D. The specimen arm is biased, for example by a spring 21, so that the specimen arm automatically returns to an elevated position away from the base plate upon release of the handle 20 of the specimen arm 4. It may be held in this position by stops (not shown).

A blade guard 23 is pivotally connected to the base plate 2 via a shaft 22 which extends through the base plate 2. When the specimen arm 4 is in its upward position, the blade guard 23 is urged against the specimen arm 4 by the force of a spring 24, thereby shielding the blade edge 14. When the specimen arm 4 is moved downwardly, contact with the contour of the front of the specimen arm 4 urges the blade guard 23 outwardly, exposing the blade edge 14 to the specimen 9.

A bore 25 is provided in the adjustment knob 7, into which a locking ball 27 is placed which is urged into locking depressions 28 of the base plate 2 by a spring 26. The depressions 28 are preferably spaced apart from one another by a predetermined distance so that by rotating the adjustment knob 7 from one depression to the adjacent depression, the specimen arm is moved a predetermined distance, a preferred distance being 5 $\mu$m.

The base plate 2 may be provided with horizontal bores 29 into which an attachment pin 30 of a screw clamp 31 can be inserted. Because of the screw clamp 31 the microtome can be quickly and reliably fastened to a sturdy work area such as a table top 32.

For the production of sections the specimen 9 is typically embedded in paraffin or plastic. This specimen is then inserted in the specimen holder recess 8 and clamped by appropriately rotating the knurled disk 12, which urges the holding plate 10 into contact with the specimen 9. Subsequently the specimen 9 may be advanced by rotating the adjustment knob 7 for the first cut. The specimen arm 4 is then grasped by the handle 20 and moved in the direction of the knife holding means 16—19 for the first cut, i.e, in the direction indicated by C. The blade guard 23 normally rests against the specimen arm 4 because of the force of the pressure spring 24, thereby preventing unintentional contact with the cutting edge 14 of the knife. When the specimen arm 4 is lowered, the blade guard is forced outwardly in the direction E, thus exposing the cutting edge 14 to enable the cut.

Upon release of the handle 20, the specimen arm 4 and the blade guard 23 return to their initial position. Before performing the next cut, the spindle 3 is typically displaced by the desired section thickness by appropriate rotation of the adjustment knob 7.

Figure 3:
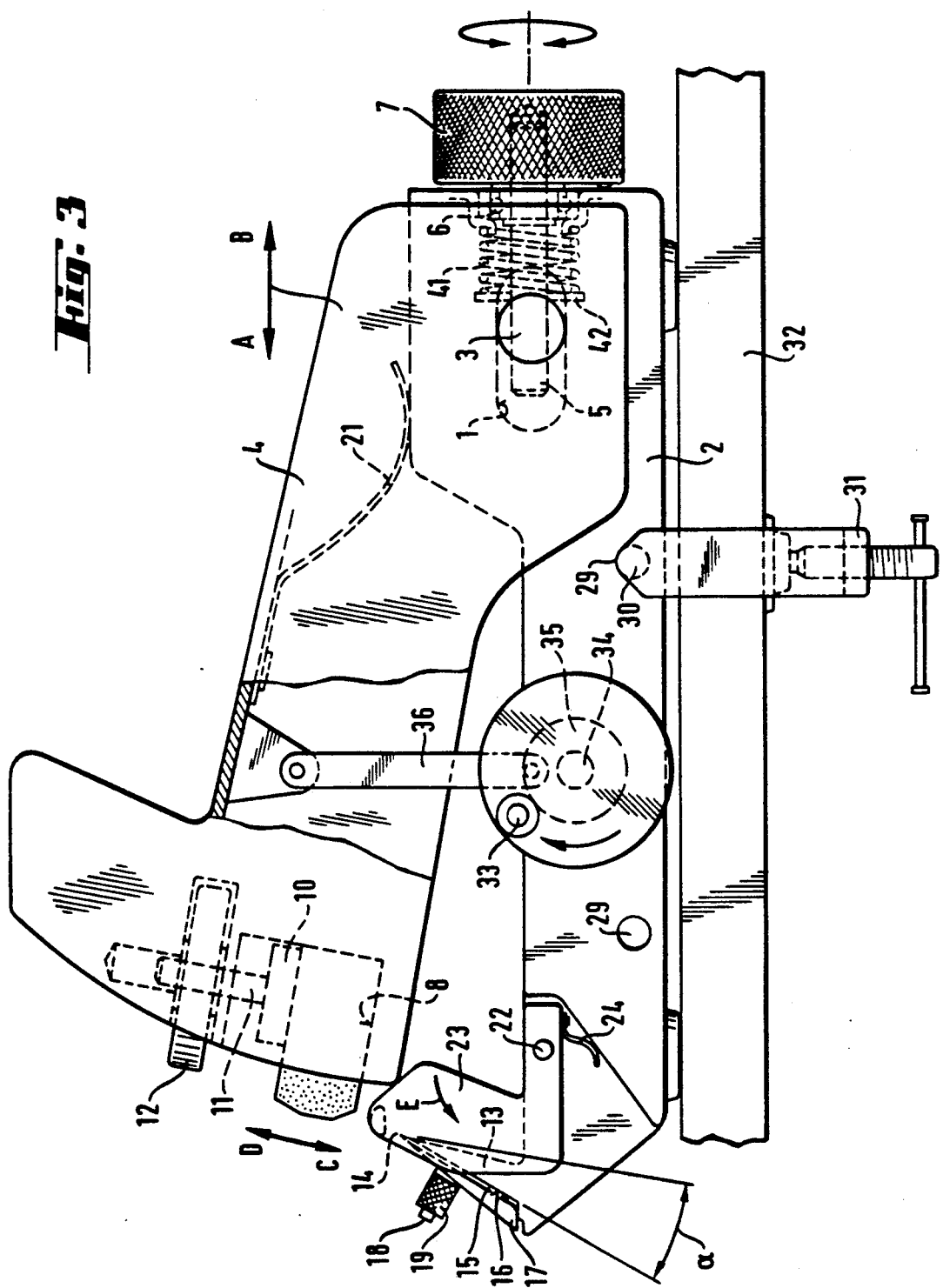
FIG. 3 is a partly sectional side view of a second embodiment of student microtome in accordance with the present invention.

FIGS. 3 and 4 refer to an alternative embodiment of the invention. Corresponding reference characters indicate parts which correspond to those of FIGS. 1 and 2, explained hereinabove. In the alternative embodiment, reciprocal movement of the specimen arm 4 is provided via a manually-rotatable crank 33 connected to a crank shaft 34 which is supported on the base plate 2. Attached to the crank shaft 34 is a crank disk 35 which is drivingly connected to the specimen arm 4 via a connecting link 36.

What is claimed is:

1. A student microtome comprising, a horizontal base, a knife holder fixed to said base adjacent to one end thereof, spindle mounting means connected to the other end of said base, a spindle having an axis and supported by said mounting means, an elongated specimen arm, one end of said specimen arm being connected to said spindle and adapted to pivot about said spindle axis, a specimen holder positioned at the distal end of said specimen arm, and adjusting means for moving said spindle relative said spindle mounting means and said knife holder.

2. A student microtome according to claim 1, wherein said spindle mounting means includes a pair of spaced, parallel members extending upwardly from said base and each of said pair has a horizontal elongated slot adapted to receive said spindle.

3. A student microtome according to claim 2, wherein said adjusting means includes a screw rotatably connected to said mounting means and a threaded bore through said spindle.

4. A student microtome according to claim 3, further including means for biasing said spindle toward said one end of said base.

5. A student microtome according to claim 2, further including incrementing means for advancing said spindle toward said knife holder in predetermined increments.

6. A student microtome according to claim 5 wherein said increment is 5 microns.

7. A student microtome according to claim 3, further including incrementing means for advancing said spindle toward said knife holder in predetermined increments.

8. A student microtome according to claim 7, wherein said increment is 5 microns.

9. A student microtome according to claim 6, wherein said incrementing means includes a knob attached to said screw, a bore spaced from said screw and extending into said knob, a ball slidably mounted in said bore, a spring urging said ball beyond the opening of said bore and a plurality of recesses in said spindle mounting means, said recesses being uniformly spaced around a circle and cooperating with said ball.

10. A student microtome according to claim 1, wherein said knife holder is adapted to hold a disposable razor blade.

11. A student microtome according to claim 1, wherein said knife holder positions the knife at an oblique angle.

12. A student microtome according to claim 11, wherein said knife holder is adapted to hold a disposable razor blade having a cutting edge.

13. A student microtome according to claim 12, wherein said knife holder includes a support surface, locating pins extending from said support surface, a pressure plate, a complementary bore in said plate for receiving each respective pin and pressure means for urging said plate toward said surface.

14. A student microtome according to claim 13, wherein of at least one of said pins is threaded and said pressure means includes at least one nut to urge the plate toward said surface.

15. A student microtome according to claim 14, wherein at least two pins locate said blade and said plate.

16. A student microtome according to claim 15, wherein said plate tapers toward said blade.

17. A student microtome according to claim 12, further including a blade guard, said blade guard being pivotally connected to said base, a spring urging said guard toward a first position shielding the blade cutting edge and said arm pivoting said guard to a second position to expose the blade cutting edge as said arm is pivoted toward said knife holder.

18. A student microtome according to claim 1, wherein said arm has a handle at said distal end for manually pivoting said arm to cut a specimen.

19. A student microtome according to claim 18, wherein said arm is spring biased away from said knife.

20. A student microtome according to claim 1, further including a manually-rotatable crank mounted on said base and a link connecting said crank to said arm at a location spaced from said spindle.

21. A student microtome according to claim 20, wherein said arm is spring biased away from said knife.

22. A student microtome according to claim 1 wherein said specimen holder includes a recess in said distal end and clamping means to hold a portion of the specimen in said recess.

23. A student microtome according to claim 22, wherein said clamping means includes a bore extending into said arm from said recess, a threaded shaft, one end of said threaded shaft having a pressure member for gripping a specimen, the other end of said threaded shaft extending into said bore, a slot extending into said distal end of said specimen arm perpendicular to said bore and a manually-rotatable, threaded nut located in said slot and cooperating with said threaded shaft to move said pressure member.

24. A student microtome according to claim 1, further including clamping means for releasably attaching said base to a support surface.

25. A student microtome according to claim 24, wherein said base has a bore and said clamping means has a pin cooperating with said bore for attaching said clamping means to said base.

26. A student microtome comprising, a horizontal base, a knife holder fixed to said base adjacent to one end thereof, said knife holder being adapted to releasably hold a disposable razor blade having a cutting edge, spindle mounting means connected to the other end of said base, a spindle having an axis and supported by said mounting means, an elongated specimen arm, one end of said specimen arm being connected to said spindle and adapted to pivot about said spindle axis, a first spring resiliently supporting the distal end of said specimen arm higher than said cutting edge, a specimen holder positioned at said distal end for moving a specimen held therein into cutting contact with said cutting edge as said arm is pivoted downward, adjusting means for moving said spindle relative to said knife holder, a blade guard pivotally connected to said base, and a second spring urging said guard toward a first position shielding the cutting edge, said arm being arranged to engage said guard as said arm is pivoted downward toward said knife holder to pivot said guard to a second position exposing the cutting edge.

* * * * *